(12) United States Patent
Larsen et al.

(10) Patent No.: US 12,329,643 B2
(45) Date of Patent: **\*Jun. 17, 2025**

(54) BONE GRAFT CAGE

(71) Applicant: DEPUY SYNTHES PRODUCTS, INC., Raynham, MA (US)

(72) Inventors: Scott Larsen, West Chester, PA (US); Ross Hamel, West Chester, PA (US); Glen Pierson, West Chester, PA (US); George Mikhail, West Chester, PA (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 1057 days.

This patent is subject to a terminal disclaimer.

(21) Appl. No.: 17/303,393

(22) Filed: May 27, 2021

(65) Prior Publication Data

US 2021/0290409 A1    Sep. 23, 2021

Related U.S. Application Data

(63) Continuation of application No. 16/670,881, filed on Oct. 31, 2019, now Pat. No. 11,051,944, which is a (Continued)

(51) Int. Cl.
*A61F 2/28*     (2006.01)
*A61F 2/30*     (2006.01)
(Continued)

(52) U.S. Cl.
CPC ............. *A61F 2/2846* (2013.01); *A61F 2/28* (2013.01); *A61F 2/30907* (2013.01);
(Continued)

(58) Field of Classification Search
None
See application file for complete search history.

(56) References Cited

U.S. PATENT DOCUMENTS 3,710,789 A    1/1973   Ersek
5,676,697 A    10/1997  McDonald
(Continued)

FOREIGN PATENT DOCUMENTS

CN    1283090    2/2001
CN    1985780    6/2007
(Continued)

OTHER PUBLICATIONS

Gugala et al., "New Approaches in the Treatment of Critical-Size Segmental defects in Long Bones", Macromol, Symp., No. 253, Wiley-VCH Verlag GmbH, & Co. KGaA, Weinheim, 2007, pp. 147-161.

*Primary Examiner* — Brian A Dukert
*Assistant Examiner* — Melissa A Hoban
(74) *Attorney, Agent, or Firm* — Fay Kaplun & Marcin, LLP

(57) ABSTRACT

A device for containing bone graft material includes an outer sleeve including a first proximal longitudinal split extending along a length thereof and a first distal longitudinal split extending along a length thereof and an inner sleeve connected to the outer sleeve via at least one strut so that a bone graft collecting space is defined therebetween, the inner sleeve including a second distal longitudinal split extending along a length thereof in combination with an interstitial mesh extending circumferentially between the inner and outer sleeves to hold graft material in the bone graft collecting space, the interstitial mesh including a third longitudinal split extending along a length thereof so that a distal side of the device may be spread open to open the distal longitudinal slot from the outer sleeve, through the interstitial mesh and the inner sleeve to a space radially within the inner sleeve.

20 Claims, 7 Drawing Sheets

Related U.S. Application Data continuation of application No. 15/617,864, filed on Jun. 8, 2017, now Pat. No. 10,507,110.

(60) Provisional application No. 62/349,470, filed on Jun. 13, 2016.

(51) Int. Cl.
  *A61F 2/46* (2006.01)
  *A61B 17/72* (2006.01)

(52) U.S. Cl.
  CPC ............ *A61F 2/4601* (2013.01); *A61B 17/72* (2013.01); *A61F 2/2803* (2013.01); *A61F 2002/2825* (2013.01); *A61F 2002/2835* (2013.01); *A61F 2002/30028* (2013.01); *A61F 2002/30062* (2013.01); *A61F 2002/30177* (2013.01); *A61F 2002/30235* (2013.01); *A61F 2002/30578* (2013.01); *A61F 2002/3071* (2013.01); *A61F 2002/30914* (2013.01); *A61F 2002/30915* (2013.01)

(56) References Cited

U.S. PATENT DOCUMENTS

| | | |
|---|---|---|
| 5,676,699 A | 10/1997 | Gogolewski et al. |
| 6,364,909 B1 | 4/2002 | McGee |
| 8,092,513 B2 | 1/2012 | Khosravi |
| 9,925,046 B2 | 3/2018 | Larsen et al. |
| 2001/0018616 A1 | 8/2001 | Schwab |
| 2002/0123750 A1 | 9/2002 | Eisermann et al. |
| 2004/0049270 A1 | 3/2004 | Gewirtz |
| 2005/0015154 A1 | 1/2005 | Lindsey et al. |
| 2005/0192675 A1 | 9/2005 | Robinson |
| 2005/0234557 A1 | 10/2005 | Lambrecht et al. |
| 2006/0282168 A1 | 12/2006 | Sherman et al. |
| 2007/0061015 A1 | 3/2007 | Jensen et al. |
| 2007/0203584 A1 | 3/2007 | Bandyopadhyay et al. |
| 2008/0269745 A1 | 10/2008 | Justin |
| 2009/0112319 A1 | 4/2009 | O'Neil et al. |
| 2010/0168771 A1 | 7/2010 | Guldberg et al. |
| 2010/0310623 A1 | 12/2010 | Laurencin et al. |
| 2011/0054408 A1 | 3/2011 | Wei et al. |
| 2011/0307073 A1 | 12/2011 | Teoh et al. |
| 2012/0029102 A1 | 2/2012 | Rose et al. |
| 2012/0029644 A1 | 2/2012 | Markworth et al. |
| 2012/0095463 A1 | 4/2012 | Rains et al. |
| 2012/0296441 A1 | 11/2012 | Mikhail et al. |
| 2013/0018482 A1 | 1/2013 | Meridew et al. |
| 2013/0261634 A1 | 10/2013 | Mckay |
| 2014/0364961 A1 | 12/2014 | Mikhail et al. |
| 2018/0193530 A1 | 7/2018 | Barbas et al. |

FOREIGN PATENT DOCUMENTS

| | | |
|---|---|---|
| CN | 101785715 | 7/2010 |
| CN | 201624812 | 11/2010 |
| CN | 102389329 | 3/2012 |
| CN | 103298429 | 9/2013 |
| CN | 103445890 | 12/2013 |
| CN | 104382636 | 3/2015 |
| CN | 107530169 | 2/2016 |
| EP | 0551611 | 7/1993 |
| EP | 1800627 | 6/2007 |
| JP | 1991176066 | 7/1991 |
| JP | 1994319794 | 11/1994 |
| JP | 2001527437 | 12/2001 |
| JP | 2014500757 | 1/2014 |
| KR | 20144/005174 | 1/2014 |
| WO | 98/38918 | 9/1998 |
| WO | 2002/064059 | 8/2002 |
| WO | 2009/025884 | 2/2009 |
| WO | 2010/011941 | 1/2010 |
| WO | 2010/044758 | 4/2010 |
| WO | 2010/093950 | 8/2010 |
| WO | 2011/094748 | 8/2011 |
| WO | 2012/068062 | 5/2012 |
| WO | 2013/006778 | 1/2013 |

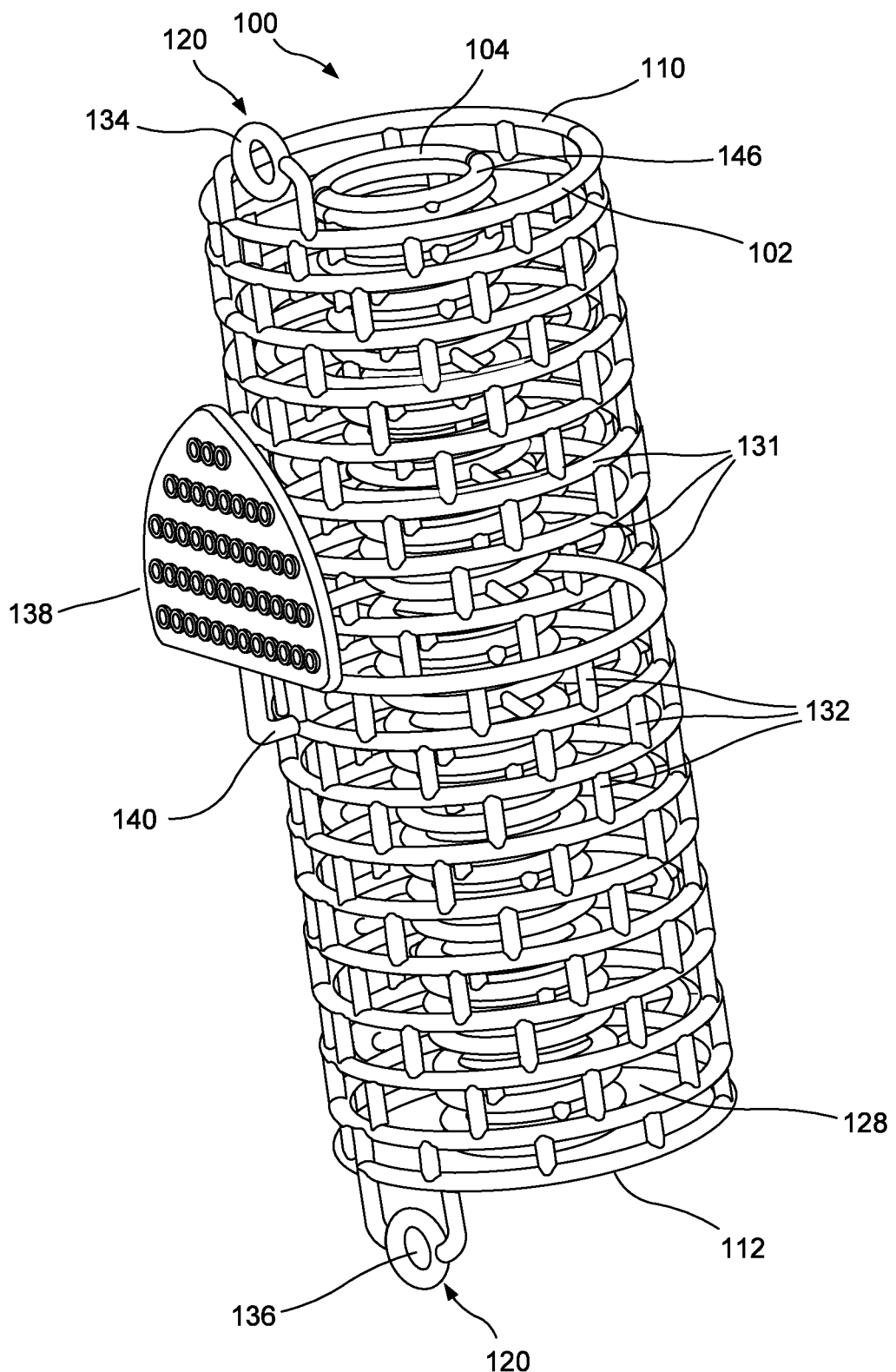
F I G. 1

BONE GRAFT CAGE

PRIORITY CLAIM

This application is a Continuation Application of U.S. patent application Ser. No. 16/670,881 filed on Oct. 31, 2019, now U.S. Pat. No. 11,051,944; which is a Continuation Application of U.S. patent application Ser. No. 15/617,864 filed on Jun. 8, 2017, now U.S. Pat. No. 10,507,110; which claims priority to U.S. Provisional Application Ser. No. 62/349,470 filed on Jun. 13, 2016. The disclosures of the above patent(s)/application(s) are incorporated herein by reference.

BACKGROUND

Large bone defects are often treated with implants and/or bone grafts to assist with healing. The bone grafts may be placed in the target area using any of a variety of methods. For example, a graft may simply be placed between two separated ends of an injured or otherwise damaged bone. However, without a container for the bone graft, the graft may fall away from a target site before it can be incorporated by the body into the healing bone. According to another method, PMMA spacers may be placed in the target area so that the fibrous tissue may be formed within the spacers. Subsequently, the PMMA spacers are removed and bone graft material is packed into the capsule formed by the body. Alternatively, some methods have included a mesh placed into the target area to contain the bone graft material at that location. These mesh containers generally include an outer wall with a diameter selected to match an outer surface of the bone to prevent the graft material from falling out of the bone.

SUMMARY OF THE INVENTION

The present invention is directed to a device for containing bone graft material including a outer sleeve extending longitudinally from a first end to a second end, the outer sleeve including a first proximal longitudinal split extending along a length thereof and a first distal longitudinal split extending along a length thereof and a inner sleeve connected to the outer sleeve via at least one strut so that a bone graft collecting space is defined therebetween, the inner sleeve including a second distal longitudinal split extending along a length thereof in combination with an interstitial mesh extending circumferentially between the inner and outer sleeves to hold graft material in the bone graft collecting space, the interstitial mesh including a third longitudinal split extending along a length thereof to form a distal longitudinal slot along the length of the device so that a distal side of the device may be spread open to open the distal longitudinal slot from the outer sleeve, through the interstitial mesh and the inner sleeve to a space radially within the inner sleeve.

BRIEF DESCRIPTION

FIG. 1 shows a perspective view of a graft containment device according to an illustrative embodiment;

DETAILED DESCRIPTION

Figure 2:
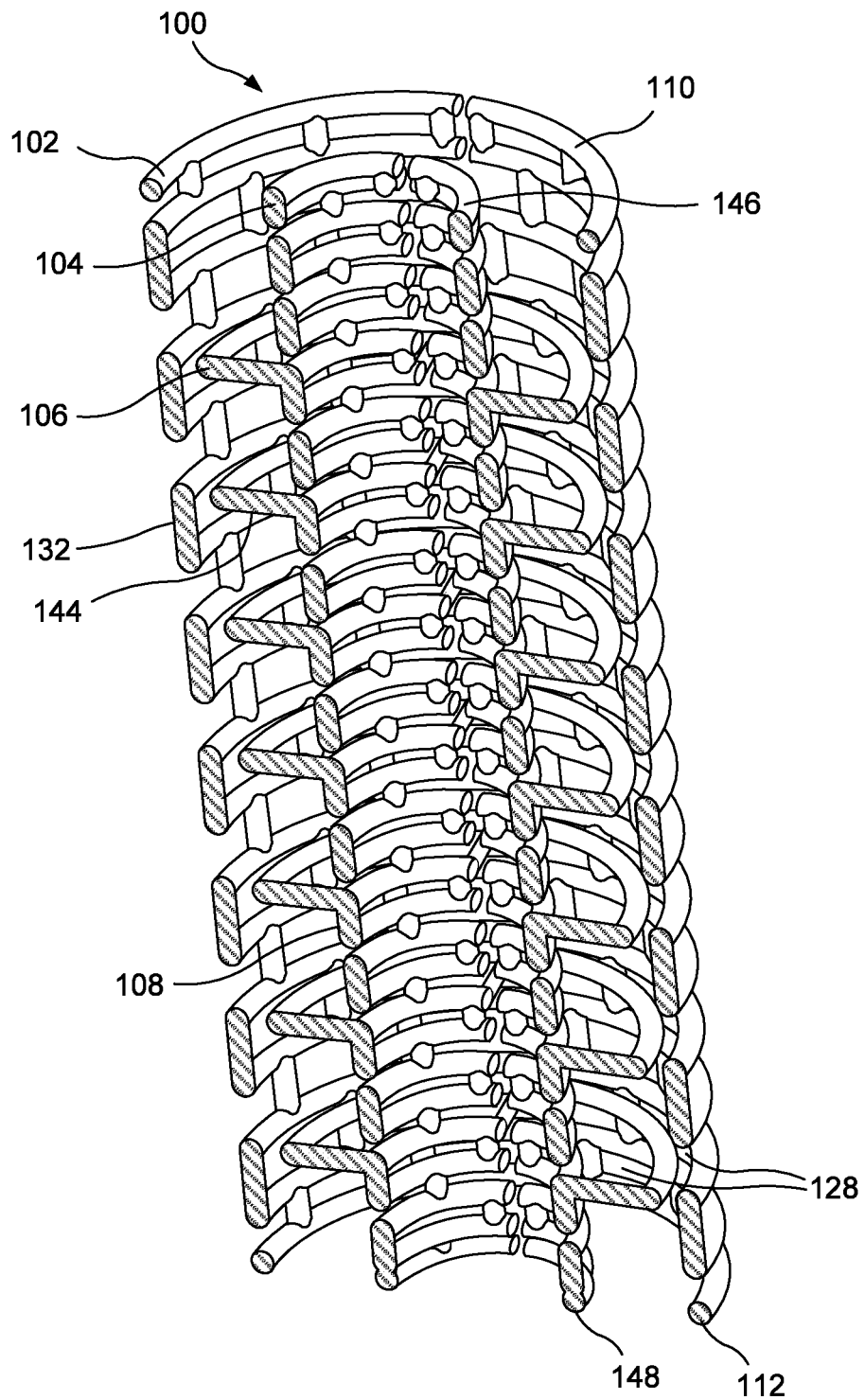
FIG. 2 shows a cross-sectional view of the device of FIG. 1.

The present invention may be further understood with reference to the following description and the appended drawings, wherein like elements are referred to with the same reference numerals. The present invention relates to the treatment of bone defects and, in particular, relates to treatments using bone graft material. Exemplary embodiments of the present invention describe a graft containment device configured to be positioned between separated longitudinal portions of a bone such that graft material may be packed therein so that healing may progress as the graft material is incorporated into new bone joining the separated portions of bone. The graft containment device of the exemplary embodiment comprises an arrangement of slots that permit a distal side of the device to be opened radially to permit insertion to a desired space between separated portions of bone over an intramedullary device so that the intramedullary device is received within an inner sleeve of the device. The outer sleeve of the device may then be radially opened on a proximal side (facing the user) to pack graft material into a space between the outer and inner sleeves. Those skilled in the art will understand that the term proximal, as used in this application, refers to a part of an item that is closer to or facing a user of the device while the term distal refers to a part of an item that is further from or facing away from a user. The device of the present invention is generally for use in treating non-articular portions of long bone such as, for example, the femur, tibia and humerus.

As shown in FIGS. 1-4, a graft containment device 100 according to an exemplary embodiment of the present invention comprises an outer sleeve 102 and an inner sleeve 104 connected to one another so that, when the device 100 is positioned in a target area between separated longitudinal portions of a target bone, the outer sleeve 102 substantially matches a profile of the outer surface of each of the separated portions of bone while the inner sleeve 104 substantially matches a profile of a medullary canal of the target bone and/or a shape of ends of the separated portions of the target bone. The device 100 also comprises an interstitial mesh 106 extending radially outward from an exterior surface 108 of the inner sleeve 104. The interstitial mesh 106 and the inner sleeve 104 hold graft material packed therein between the outer and inner sleeves 102, 104 and prevent migration of the device 100 along the length of the bone once the device 100 has been positioned in the target area between the separated portions of bone. The outer sleeve 102, inner sleeve 104 and the interstitial mesh 106 of the device 100 are formed via a strut framework so that the device 100 may be three dimensionally built (e.g., by 3-D printing) using patient specific bone dimensions, which may be obtained, for example, via 3D imaging of the target bone. In particular, circumferential and/or axial driver curves, along with a desired spacing between adjacent struts, may be used as input data for building and printing the device 100.

The outer sleeve 102 extends longitudinally from a first end 110 to a second end 112 and, in this embodiment, defines a generally cylindrical shape corresponding to the profile of the outer surface of the target bone. The device 100 includes a distal longitudinal slot 114 extending radially through the outer and inner sleeves 102, 104, respectively, along an entire length of the device 100 so that the device 100 may be opened to be slid over a medullary rod (or other insert) extending between the separated segments of bone. This permits the device 100 to be slid directly over the rod between the separated segments of bone so that the rod ends up radially within an inner space 115 defined by the inner sleeve 104. In other words, struts 116 and 116' extend from the inner sleeve 104 to the outer sleeve 102 and are separated circumferentially from one another to define the longitudinal slot 114. Those skilled in the art will understand that the device 100 may include any number of struts 116 and 116' separated from one another longitudinally along the length of the device 100 (i.e., from the first end 110 to the second end 112) to sufficiently couple the inner sleeve 104 to the outer sleeve 102 while permitting the device 100 to open circumferentially as desired. In this embodiment, the struts 116, 116' form the only connection between the outer sleeve 102 and the inner sleeve 104. This permits the outer sleeve 102 to be opened circumferentially to a large extent to facilitate the packing of graft material therein. However, those skilled in the art will understand that additional connections may be made at selected points around the circumference of the device 100 to enhance the structural integrity of the device although this may reduce the amount by which the outer sleeve 102 may be spread open to pack the graft material therein. Thus, the device 100 may be spread open at the slot 114 to permit an intramedullary rod or other implant to be slid into the device 100 as will be described in more detail below. As will be understood by those skilled in the art, the first and second ends 110, 112, respectively, of the outer sleeve 102 of this embodiment are separated by a distance substantially equal to a distance by which the portions of bone are separated. As would be understood by those skilled in the art, the first and second ends 110, 112 need not be flat and do not need to have the same general shape. Each of the first and second ends 110, 112 may take any shape necessary to conform to the shape of the end of the separated portion of bone to which it will be adjacent. This allows the outer sleeve 102 and the inner sleeve 104 to abut ends of both of the separated segments of bone. However, alternatively, a length of the outer sleeve 102 may extend slightly beyond the length of the inner sleeve 104 so that the outer sleeve 102 over laps one or both of the ends of the separated portions of bone. The device 100 according to this embodiment also includes a projection 120 at each of the first and second ends 110, 112, respectively, with each of the projections 120 including a hole through which a screw or other fastener may be inserted to couple the device 100 to the bone. Those skilled in the art will recognize that either or both of these projections 120 may be omitted in favor of other means for securing the device 100 to the bone.

The device 100 according to this embodiment also includes an inner slot 118 formed in the inner sleeve 104 diametrically opposed to the slot 114. This inner slot 118 enhances the ability of the inner sleeve 104 to spread circumferentially permitting the device 100 to be more easily opened to the extent necessary to facilitate the insertion of the device 100 over a medullary rod. Those skilled in the art will understand that this inner slot 118 is optional and may be omitted in any device that is sufficiently flexible to accommodate a medullary rod or other implant with which it is to be employed without the slot 118. Specifically, the slot 114 allows a surgeon to insert the device 100 with the distal side 124 of the device 100 (including the slot 114) facing the bone. The surgeon may then spread the distal side 124 of the device 100 open circumferentially to slide the device 100 over an intramedullary rod and into position between the separated portions of bone. During insertion, the proximal side 122 of the device 100 faces the surgeon who may then use proximal slot 126 to spread open the outer sleeve 102 so that he may pack bone graft material into the annular space 128 between the outer and inner sleeves 102, 104, respectively, from the proximal side of the device 100.

Specifically, to properly insert the device 100 into the space between portions of a bone separated from one another longitudinally (i.e., along an axis of the bone) when a medullary rod extends between these portions of bone, the distal side of the device 100 is opened circumferentially via the distal slot 114 and the intramedullary rod is passed through the slot 114 until it enters the inner space 115 within the inner sleeve 104. The surgeon then allows the device 100 to close circumferentially (e.g., under its natural bias or by pushing it closed). Those skilled in the art will understand that, after the device 100 has been positioned as desired, it will be held in the closed position by the surrounding soft tissues. In addition, after the procedure has been completed, the proximal side 122 of the device 100 may then be closed, for example, by suturing. After the device 100 has been positioned as desired (but before the proximal side 122 of the device 100 is sutured closed, the surgeon then spreads the outer sleeve 102 open circumferentially by spreading apart the halves of the outer sleeve 102 separated by the proximal slot 126. This permits the surgeon to pack the annular space 128 with bone graft material or, if the space was already packed with graft material, to supplement this material with additional graft (e.g., to replace any material that may have been lost as the device 100 was positioned).

The outer sleeve 102 is coupled to the struts 116 and 116' at joints 130, 130' that are formed to permit the outer sleeve 102 to flex and pivot relative to the struts 116, 116'. That is, the joints 130, 130' permit the halves of the outer sleeve 102 to rotate relative to the struts 116, 116', respectively, when the surgeon spreads the halves of the outer sleeve 102 apart circumferentially to open the slot 126. As would be understood by those skilled in the art, the joints 130, 130' in this embodiment form a living hinge to permit the desired rotation of the outer sleeve 102 relative to the struts 116, 116'. The struts 116, 116' of this embodiment are also connected to the interstitial mesh 106 so that, when the halves of the outer sleeve 102 are spread away from one another at the slot 114, the entire device is spread open—i.e., the outer sleeve 102, the interstitial mesh 106 and the inner sleeve 104 are spread open so that an intramedullary rod may be passed all the way to the space 115 within the inner sleeve 104.

As would be understood by those skilled in the art, the outer sleeve 102 is built via a strut framework so that the outer sleeve 102 is formed in a mesh configuration. The mesh configuration of the outer sleeve 102 of the embodiment shown in FIGS. 1-4 includes circumferential struts 131 and axial struts 132 intersecting one another. Adjacent circumferential struts 130 and adjacent axial struts 132 may be separated from one another by a distance of between 0.4 mm to 10.0 mm or any other distance desired that will provide the desired structural integrity of the device 100 and a desired level of containment for the graft material therein. The circumferential and axial struts 131, 132 may intersect one another to form any of a variety of mesh patterns. In one embodiment, the circumferential and axial struts 131, 132 may intersect one another to form a substantially grid-like pattern. In another embodiment, as shown in FIG. 1, circumferential struts 131 may be connected to one another via axial struts 132, which are alternatingly interrupted along a length thereof to form a staggered mesh pattern. The staggered mesh pattern may be particularly useful for controlling both the containment of the graft material between the inner and outer sleeves 104, 102 as well as a flexibility of the device 200. A distance between adjacent circumferential struts 131 controls the containment of the graft material while the alternating axial struts 132 adjacent circumferential struts 131 control the flexibility (e.g., torsional and axial) of the device 100. The axial struts 132 prevent buckling of the device 100.

In particular, the axial struts 132 are interrupted between adjacent circumferential struts 131 so that openings defined by the interesting struts 131, 132 are offset from one another about a circumference of the device in a staggered pattern. This permits portions of adjacent circumferential struts 131 extending between connecting axial struts 132 to be compressed toward one another to provide axial and/or torsional flexibility. Thus, the larger the distance between axial struts 132, the greater the flexibility. In one embodiment, the distance between adjacent axial struts 132 may be larger than a distance between adjacent circumferential struts 131. It will be understood by those of skill in the art, however, that a distance between adjacent struts may be varied, as desired, and is not required to be constant along an entire length and/or about an entire circumference of the device 100. As would be understood by those skilled in the art, the inner sleeve 104 may be constructed in the same manner including circumferential and axial struts with a similar or different separation as desired.

As described above, the length of the outer sleeve 102 may be selected so that first and second ends 110, 112 of the outer sleeve 102 abut the separated ends of the target bone or so that the ends 110, 112 overlap the separated ends of the target bone by a desired length. In addition, one or both of the ends 110, 112 may include a screw receiving structure 134 projecting axially away from the corresponding one of the ends 110, 112 to position a screw hole 136 thereof at a desired position on the corresponding portion of the target bone. In addition, the device 100 may include a tag 138 connected to the outer sleeve 102 via a separable strut 140. As would be understood by those skilled in the art, the tag may display any desired information (e.g., information as to whether one or more cages are to be used, lot number, surgeon name, etc.) while also indicating a desired implantation position (e.g., via text and/or shape with a pointed end of the tag facing a superior end of the bone), as well as a desired orientation with respect to rotation of the device 100 about its longitudinal axis (e.g., with the tag 138 being mounted on a proximal side 122 of the device 100). When the device 100 has been positioned as desired, the tag 138 may be separated from the device 100 (e.g., by snipping the strut 140).

The inner sleeve 104 is connected to the interstitial mesh 106 via a plurality of members 144 so that the inner and outer sleeves 104, 102 are separated from one another via the annular space 128. The inner sleeve 104 extends longitudinally from a first end 146 to a second end 148 and, as described above, defines a shape substantially corresponding to a medullary canal of the target bone and has a length substantially corresponding to the distance of separation between the separated portions of bone. As would be understood by those skilled in the art, wherein length of the outer sleeve 102 is selected to be equal to a distance between the separated portions of bone, the inner sleeve 104 and the outer sleeve 102 with have the same length. If the outer sleeve 102 is lengthened to overlap at one or both ends of the device 100, the inner sleeve 104 will be slightly shorter than the outer sleeve 102. Connecting the inner sleeve 104 to the outer sleeve 102 only via the struts 116, 116' permits the inner sleeve 104 to float within the outer sleeve 102. Thus, if the device 100 is being utilized with a target bone having an intramedullary rod implanted therein, as described above, the inner sleeve 104 is movable relative to the outer sleeve 102 to find the intramedullary rod for cases in which the intramedullary rod is not centered.

Figure 3:
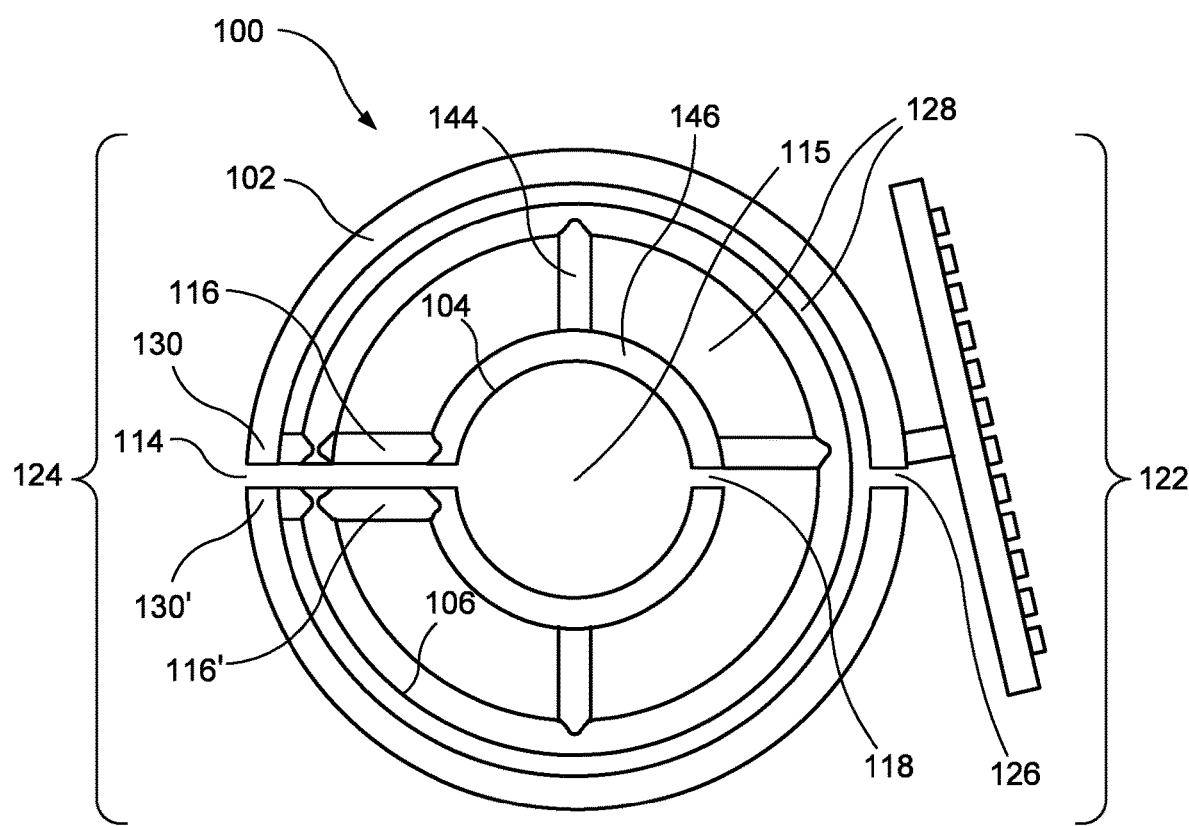
FIG. 3 shows an end view of the device of FIG. 1.
Figure 4:
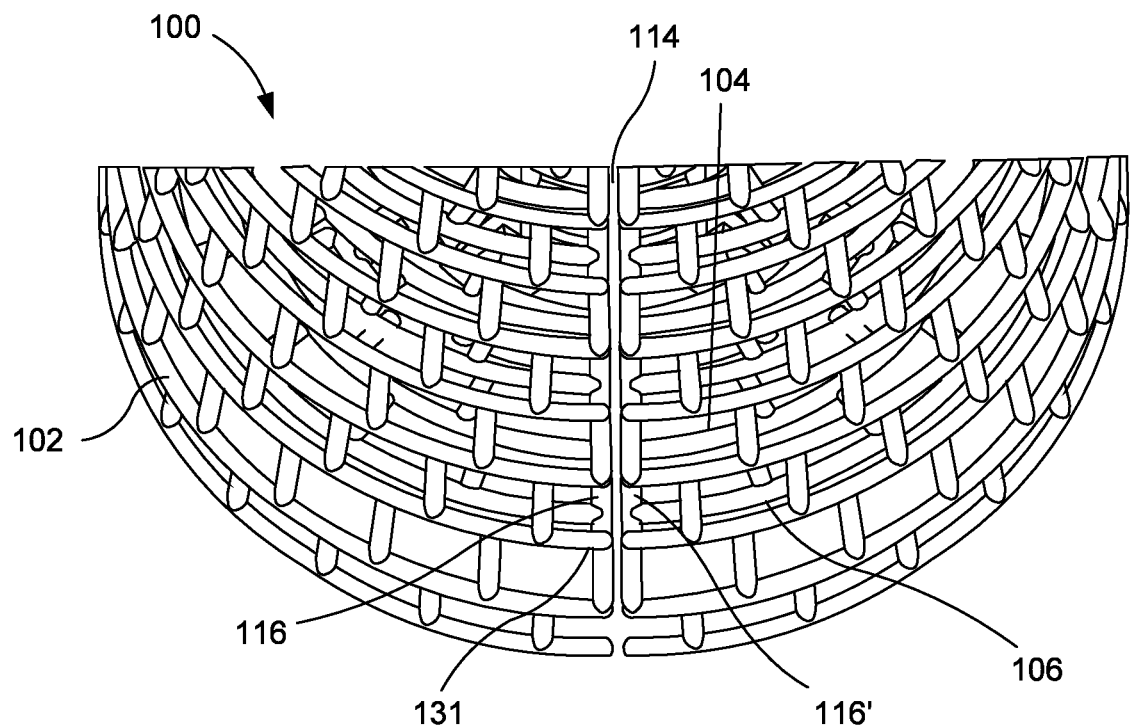
FIG. 4 shows an enlarged perspective view of the device of FIG. 1.
Figure 5:
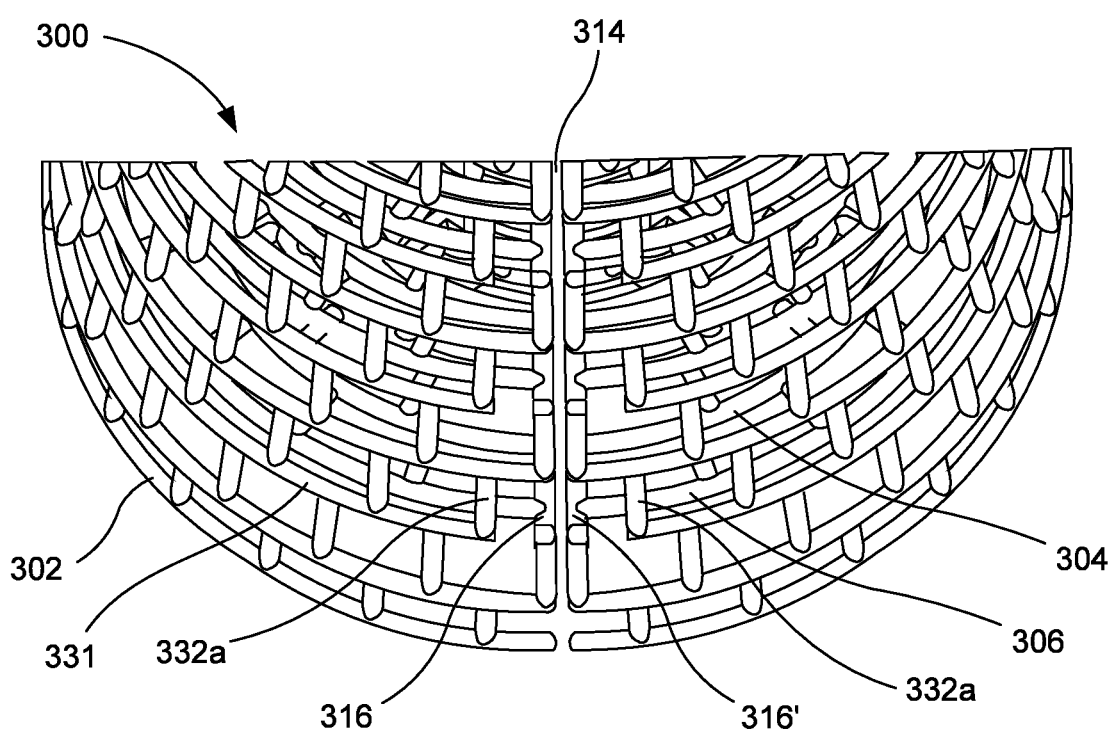
FIG. 5 shows an enlarged perspective view of a graft containment device according to an alternate embodiment.

In one embodiment, as shown in FIGS. 3-4, in which the outer and inner sleeves 102, 104 are formed via a staggered mesh pattern, each of the struts 116, 116' extends from a circumferential strut 131 of the outer sleeve 102 to a corresponding circumferential strut of the inner sleeve 104 so that joints 130, 131' connecting the outer sleeve 102 to the struts 116, 116' are formed at ends of each of the struts 116, 116'. In other words, each strut 116, 116' is connected to one of the circumferential struts 131 of the outer sleeve 102. As described above, the interstitial mesh 106 is also connected to these struts 116, 116' so that the entire device 100 may be spread open via the distal slot 114. It will be understood by those of skill in the art, however, that the outer and inner sleeves 102, 104 may be connected to one another via the struts 116, 116' in any of a variety of configurations. For example, in an alternate embodiment as shown in FIG. 5, struts 316, 316' extending between outer and inner sleeves 302, 304 of a graft containment device 300 may connect a circumferential strut of the inner sleeve 304 to the interstitial mesh 306 without connecting directly to a corresponding circumferential strut 331 of the outer sleeve 302. In other words, a portion of the corresponding circumferential strut 331 extending between an axial strut 332a immediately adjacent to a distal slot 314 may be removed to create a torsion type flexural hinge rather than a bending type flexural hinge 130, 131', as described above in regard to the device 100.

Since the device 100 may be custom built and printed for a specific patient, the length, circumference and shape of the outer sleeve 102 may be customized. For example, the length of the outer sleeve 102 may be selected so that, when the outer sleeve 102 is positioned in the target area about the target bone, first and second ends 110, 112 of the outer sleeve 102 match the distance separating the portions of bone or so that they overlap the bone by, for example, 5 mm on each side. The length of the inner sleeve 104 may be selected so that there is a clearance between the end surfaces of the separated portions of bone by a selected distance (e.g., 2 mm at the first and second ends 146, 148 of the inner sleeve 104). It will be understood by those of skill in the art, however, that dimensions of the device 100 may be varied, as desired and suited for a specific patient. The device 100 may be formed of biodegradable polymers such as, for example, polycaprolactone (PCL), which is both printable and bioresorbable.

According to an exemplary method, the device 100 may be custom-built and printed to suit patient specific bone dimensions and needs. In particular, a target bone of a patient may be imaged to obtain bone dimensions such as, for example, circumferences of both an outer surface and an inner surface (i.e., corresponding to a medullary canal) of a desired portion of the target bone, along with a length of a portion of the bone to be treated (i.e., a distance between separated portions of the target bone). These dimensions may be used to enter input data to build and print the device 100 using, for example, CAD software. Once the device 100 has been built, as described above, the device 100 may be positioned in the target area between separated portions of the target bone.

In particular, the device 100 which may have been previously packed with graft material may be oriented as desired (e.g., by reference to the tag 138 with the distal side 124 of the device 100 facing the target bone in which an intramedullary rod has been inserted. The outer sleeve 102, interstitial mesh 106 and the inner sleeve 104 may then be opened by separating spreading the device open via the slot 114. The device 100 may then be slid between the separated portions of bone until the intramedullary rod is received in the space 115. At this point, the device 100 may be released to permit the slot 114 to close. The surgeon may then remove the tag 138 and open the outer sleeve 102 at the proximal side 122 of the device 100 to pack additional graft material into the space 128 via the widened slot 126. Those skilled in the art will understand that this embodiment allows the surgeon to open the device 100 via the slot 114 at the distal side 124 to slide the device 100 into position over an intramedullary rod while permitting the surgeon to open the device 100 via the slot 126 on the proximal side of the device 100 to pack additional graft material therein without rotating the device 100. This may be especially useful in a case where the inner and or outer sleeves 104, 102, respectively, are asymmetrical from the proximal side 122 to the distal side 124. For example, if the distal side 124 of the device 100 is shorter than the proximal side 122 (reflecting a similar asymmetry in the separated portions of bone), the device 100 can only be inserted distal side first which would make the split inaccessible for later packing of graft material. Thus, a device such as the device 100 with a distal split at the slot 114 and a proximal split at the slot 126 could be inserted distal side first to capture the intramedullary rod and, when the device has reached the desired position between the separated portions of bone, the user may pack additional graft material into the device in a way that would not be feasible without the proximal slot 126.

Graft material may also be inserted at the ends of the device 100, between the first and second ends 146, 148 of the inner sleeve 104 and the ends of the separated portions of bone. Once the device 100 has been positioned as desired, the outer sleeve 102 may be closed by drawing the longitudinal edges of the outer sleeve 102 adjacent to the slots 114 and 126 toward one another and fixing these edges to one another. For example, the longitudinal edges may be sutured together to fix the device 100 over the target bone. Additional graft material may be packed into device via the mesh of the outer sleeve 102 after the device 100 has been positioned over the bone, as described above.

The overlapping of the first and second ends 110, 112 over ends of the separated portions of bone and the positioning of the inner sleeve 104 between two portions of bone is sufficient to hold the device 100 in position over the target area of the bone. In particular, the interstitial mesh 106 and the inner sleeve 104 help to prevent migration of the device 100 along the bone. In some cases where additional fixation is desired, however, a user (e.g., surgeon) may insert a bone fixation element (e.g., a bone screw) through one or more of the screw holes 136 formed in the screw receiving structures 134 into the underlying bone.

In some cases, the user may desire to further customize the device 100 during the grafting process. In these cases, the user may cut portions of the device 100 to accommodate the specific needs of the patient's bone. The device 100 may be formed of a material that may be cut using, for example, a scissor or other cutting tool. For example, if desired, the user may adjust a length of the outer sleeve 102 to suit a patients' specific needs and/or to create less overlap between the device 100 and the bone.

Figure 7:
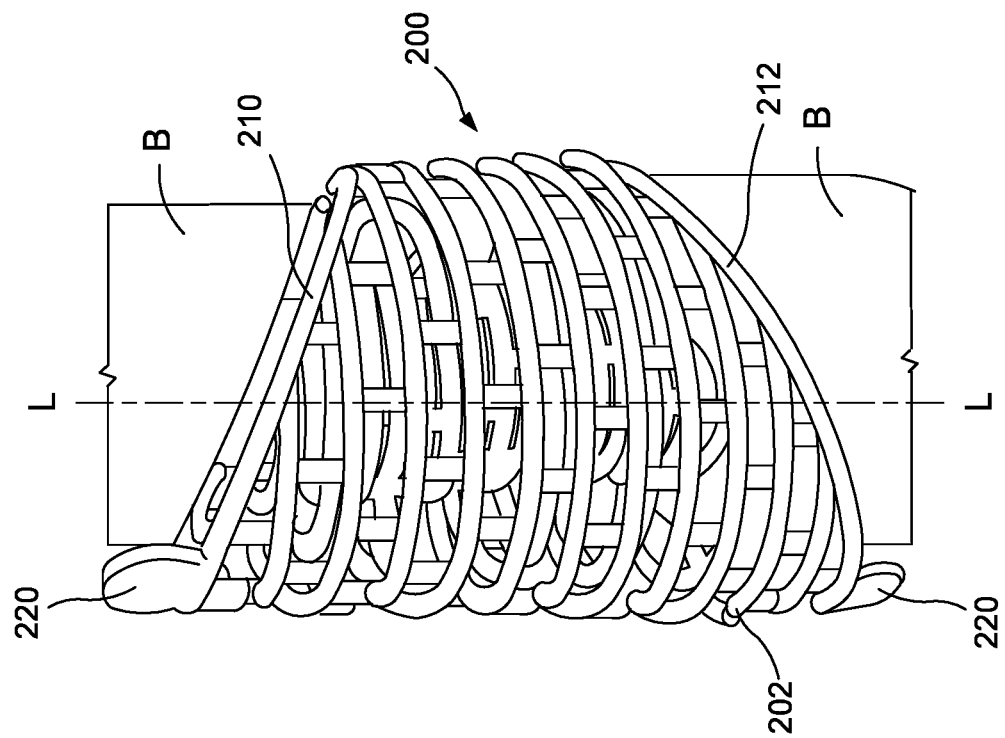
FIG. 7 shows a perspective view of the graft containment device of FIG. 6, in a desired final position between the two separated portions of bone.
Figure 6:
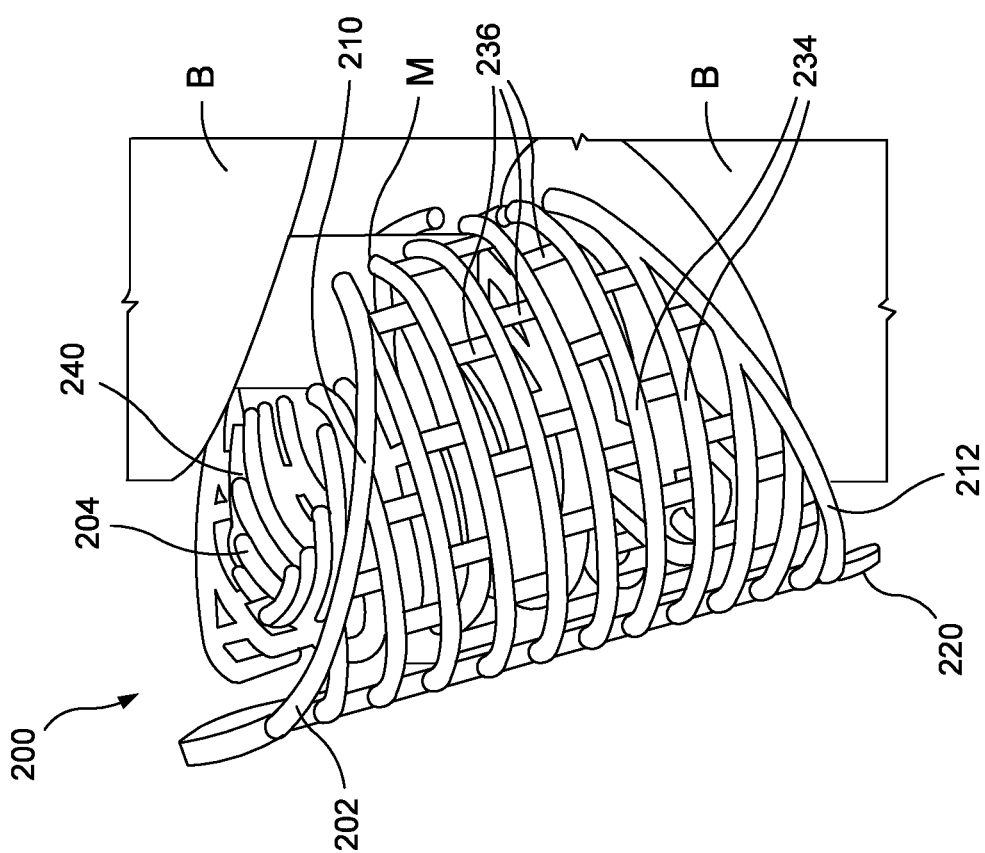
FIG. 6 shows a perspective view of a graft containment device according to a further embodiment partially inserted over an intramedullary rod between two separated portions of bone.
Figure 8:
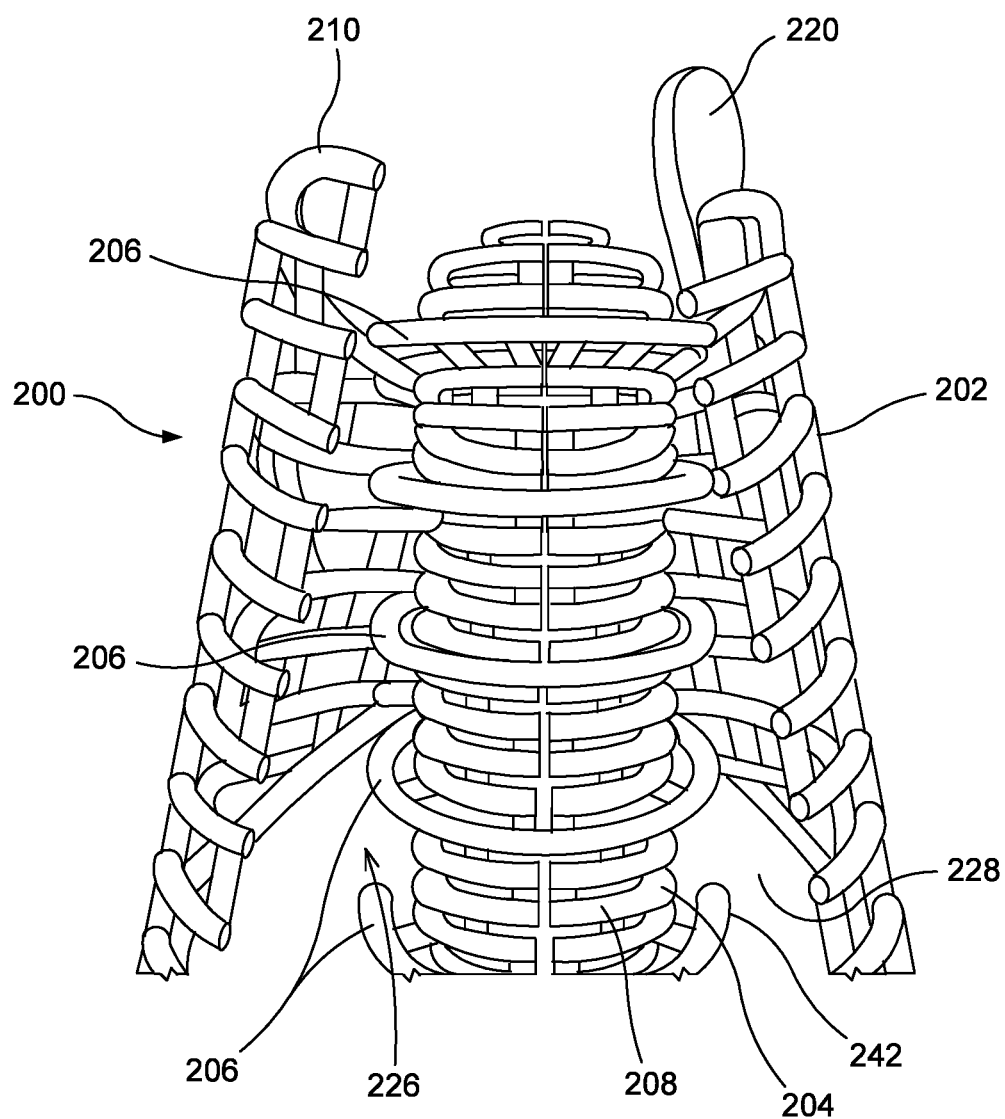
FIG. 8 shows a perspective view of the graft containment device of FIG. 6 with an outer sleeve thereof spread open.

FIGS. 6-9 show a graft containment device 200 according to a further embodiment of the invention that is substantially similar to the device 100 described above except as indicated below. Specifically, the device 200 includes first and second ends 210, 212 angled relative to a longitudinal axis L of the device 200 to match a contour of the separated ends of the bone B between which the device 200 will be positioned. Thus, the device 200, when positioned as desired between the separated portions of bone B may be filled with bone graft material so that the bone graft material may be held in position between the separated portions of bone B until it has been incorporated into the bone B. In addition, as shown in FIGS. 6 and 7, an intramedullary rod M extends through the medullary canal of the bone B and across the gap separating the portions of bone B to connect these portions of bone B to one another. The device 200 comprises an outer sleeve 202 and an inner sleeve 204 connected to one another so that, when the device 200 is positioned in a target area between separated longitudinal portions of a target bone B, the outer sleeve 202 substantially matches a profile of the outer surface of each of the separated portions of bone B while the inner sleeve 204 substantially matches a profile of a medullary canal of the target bone and/or a shape of ends of the separated portions of the target bone B. The device 200 also comprises an interstitial mesh 206 extending radially outward from an exterior surface 208 of the inner sleeve 204. The interstitial mesh 206 and the inner sleeve 204 hold graft material packed therein between the outer and inner sleeves 202, 204 and prevent migration of the device 100 along the length of the bone B once the device 200 has been positioned in the target area between the separated portions of bone B. Similarly to the device 100, the outer and inner sleeves 202, 204 may be formed of a mesh structure and, in one particular embodiment, may be formed of a staggered mesh pattern, as described above with respect to the outer sleeve 102. The outer sleeve 202, inner sleeve 204 and the interstitial mesh 206 of the device 200 are formed via a strut framework so that the device 200 may be three dimensionally built (e.g., by 3-D printing) using patient specific bone dimensions, which may be obtained, for example, via 3D imaging of the target bone. In particular, circumferential and/or axial driver curves, along with a desired spacing between adjacent struts, may be used as input data for building and printing the device 200.

Figure 9:
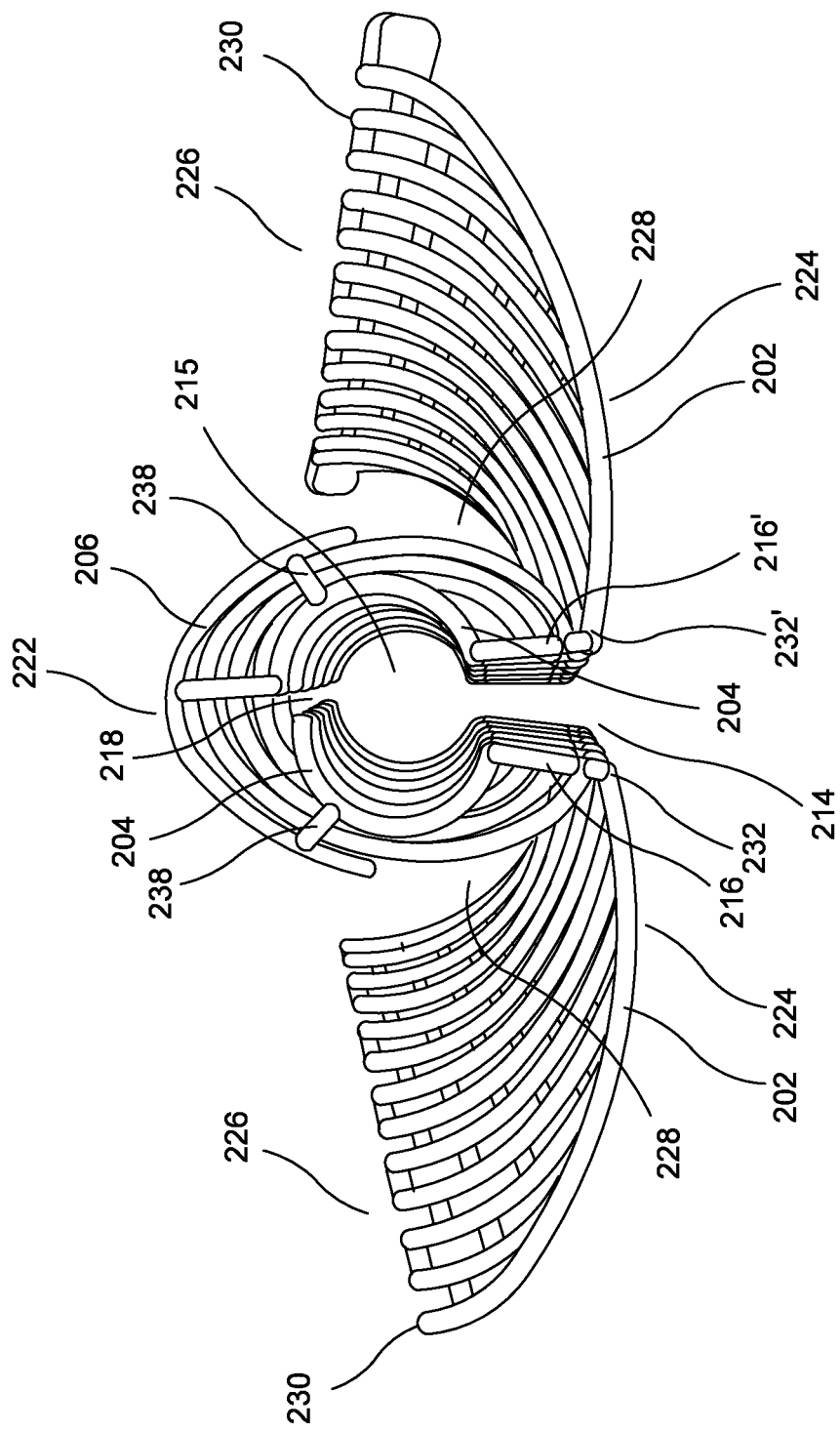
FIG. 9 shows an end view of the graft containment device of FIG. 6 with the outer sleeve thereof spread open and a longitudinal slot thereof partially opened.

The outer sleeve 202 extends longitudinally from a first end 210 to a second end 212 and, in this embodiment, defines a generally cylindrical shape with angled ends corresponding to the profile of the outer surface of the target bone. The device 200 includes a distal longitudinal slot 214 extending radially through the outer and inner sleeves 202, 204, respectively, along an entire length of the device 200 so that the device 200 may be opened to be slid over a medullary rod M (or other insert) extending between the separated segments of bone B. This permits the device 200 to be slid directly over the rod M between the separated segments of bone B so that the rod M ends up radially within an inner space 215 defined by the inner sleeve 204. In other words, struts 216 and 216' extend from the inner sleeve 204 to the outer sleeve 202 and are separated circumferentially from one another to define the longitudinal slot 214. Those skilled in the art will understand that the device 200 may include any number of struts 216 and 216' separated from one another longitudinally along the length of the device 200 (i.e., from the first end 210 to the second end 212) to sufficiently couple the inner sleeve 204 to the outer sleeve 202 while permitting the device 200 to open circumferentially as desired. In this embodiment, the struts 216, 216' form the only connection between the outer sleeve 202 and the inner sleeve 204. This permits the outer sleeve 202 to be opened circumferentially to a large extent (as shown in FIG. 9) to facilitate the packing of graft material therein. However, those skilled in the art will understand that additional connections may be made at selected points around the circumference of the device 200 to enhance the structural integrity of the device 200 although this may reduce the amount by which the outer sleeve 202 may be spread open to pack the graft material therein. Thus, the device 200 may be spread open at the slot 214 to permit an intramedullary rod M or other implant to be slid into the device 200 as will be described in more detail below. As will be understood by those skilled in the art, the first and second ends 210, 212, respectively, of the outer sleeve 202 of this embodiment are separated by a distance substantially equal to a distance by which the portions of bone are separated. As would be understood by those skilled in the art, the first and second ends 210, 212 need not be flat and do not need to have the same general shape. Each of the first and second ends 210, 212 may take any shape necessary to conform to the shape of the end of the separated portion of bone to which it will be adjacent. This allows the outer sleeve 202 and the inner sleeve 204 to abut ends of both of the separated segments of bone B. However, alternatively, a length of the outer sleeve 202 may extend slightly beyond the length of the inner sleeve 204 so that the outer sleeve 202 over laps one or both of the ends of the separated portions of bone B. The device 200 according to this embodiment also includes a projection 220 at each of the first and second ends 210, 212, respectively, with each of the projections 220 including a hole (not shown) through which a screw or other fastener may be inserted to couple the device 200 to the bone. Those skilled in the art will recognize that either or both of these projections 220 may be omitted in favor of other means for securing the device 200 to the bone B.

Although the exemplary method describes the device 200 as utilized with a target bone B having an intramedullary rod M implanted therein, it will be understood by those of skill in the art that the intramedullary rod M is not a requirement of the device 200. The device 200 may also be utilized with other bone fixation implants such as, for example, a bone plate. Where the device 200 is being used with a bone plate rather than an intramedullary rod M the inner sleeve 204 may simply be fixed in a closed configuration via, for example, suturing, prior to closing the outer sleeve 202 about the target bone B. Alternatively, although the inner sleeve 204 is shown and described as forming two clamshell portions separated at the slot 214 and the inner slot 218, the inner slot 218 may be replaced by a living hinge or other structure that allows the inner sleeve 204 to flex open as necessary to receive the intramedullary rod.

The device 200 according to this embodiment also includes an inner slot 218 formed in the inner sleeve 204 diametrically opposed to the slot 214. This inner slot 218 enhances the ability of the inner sleeve 204 to spread circumferentially permitting the device 200 to be more easily opened to the extent necessary to facilitate the insertion of the device 200 over the medullary rod M. Those skilled in the art will understand that this inner slot 218 is optional and may be omitted in any device that is sufficiently flexible to accommodate a medullary rod or other implant with which it is to be employed without the slot 218. Specifically, the slot 214 allows a surgeon to insert the device 200 with the distal side 224 of the device 200 (including the slot 214) facing the bone B. The surgeon may then spread the distal side 224 of the device 200 open circumferentially to slide the device 200 over the intramedullary rod M and into position between the separated portions of bone B. During insertion, the proximal side 222 of the device 200 faces the surgeon who may then use proximal slot 226 to spread open the outer sleeve 202 so that he may pack bone graft material into the annular space 228 between the outer and inner sleeves 202, 204, respectively, from the proximal side of the device 200.

Specifically, to properly insert the device 200 into the space between portions of the bone B separated from one another longitudinally (i.e., along an axis of the bone) with the medullary rod M extending between these portions of bone B, the distal side of the device 200 is opened circumferentially via the distal slot 214 and the intramedullary rod M is passed through the slot 214 until it enters the inner space 215 within the inner sleeve 204. The surgeon then allows the device 20 to close circumferentially (e.g., under its natural bias or by pushing it closed). Those skilled in the art will understand that, after the device 200 has been positioned as desired, it will be held in the closed position by the surrounding soft tissues. In addition, after the procedure has been completed, the proximal side 222 of the device 200 may then be closed permanently, for example, by suturing. After the device 200 has been positioned as desired (but before the proximal side 222 of the device 200 has been sutured closed, the surgeon then spreads the outer sleeve 202 open circumferentially by spreading apart the halves 230 of the outer sleeve 202 separated from one another by the proximal slot 226. This permits the surgeon to pack the annular space 228 with bone graft material or, if the space was already packed with graft material, to supplement this material with additional graft (e.g., to replace any material that may have been lost as the device 200 was positioned).

The outer sleeve 202 is coupled to the struts 216 and 216' at joints 232, 232' that are formed to permit the outer sleeve 202 to flex and pivot relative to the struts 216, 216'. That is, the joints 232, 232' permit the halves of the outer sleeve 202 to rotate relative to the struts 216, 216', respectively, when the surgeon spreads the halves 230 of the outer sleeve 202 apart circumferentially to open the slot 226. As would be understood by those skilled in the art, the joints 232, 232' in this embodiment form a living hinge to permit the desired rotation of the outer sleeve 202 relative to the struts 216, 216'. The struts 216, 216' of this embodiment are also connected to the interstitial mesh 206 so that, when the halves 230 of the outer sleeve 202 are spread away from one another at the slot 214, the entire device is spread open—i.e., the outer sleeve 202, the interstitial mesh 206 and the inner sleeve 204 are spread open so that the intramedullary rod M may be passed all the way into the space 215 within the inner sleeve 204.

Although the outer and inner sleeves 202, 204 of the device 200 are shown and described as formed of circumferential and axial struts that intersect one another, it will be understood by those of skill in the art that the outer and inner sleeves 202, 204 may be formed of any of a variety of mesh structures and patterns so long as the device 200 is formed via a strut framework that will sufficiently contain graft material packed therein.

As would be understood by those skilled in the art, the outer sleeve 202 is built via a strut framework so that the outer sleeve 202 is formed in a mesh configuration. The mesh configuration of the outer sleeve 202 of the embodiment shown in FIGS. 6-9 includes circumferential struts 234 and axial struts 236 intersecting one another. Adjacent circumferential struts 234 and adjacent axial struts 236 may be separated from one another by a distance of between 0.4 mm to 10.0 mm or any other distance desired that will provide the desired structural integrity of the device 200 and a desired level of containment for the graft material therein. As would be understood by those skilled in the art, the inner sleeve 204 may be constructed in substantially the same manner including circumferential and axial struts with a similar or different separation as desired. As described above, the length of the outer sleeve 202 may be selected so that first and second ends 210, 212 of the outer sleeve 202 abut the separated ends of the target bone B or so that the ends 210, 212 overlap the separated ends of the target bone B by a desired length. In addition, one or both of the ends 210, 212 may include a screw receiving structure 220 projecting axially away from the corresponding one of the ends 210, 212 to position a screw hole (not shown) thereof at a desired position on the corresponding portion of the target bone B. In addition, the device 200 may include a tag (not shown) as described above displaying any desired information (e.g., information as to whether one or more cages are to be used, lot number, surgeon name, etc.) while also indicating a desired implantation position (e.g., via text and/or shape with a pointed end of the tag facing a superior end of the bone), as well as a desired orientation with respect to rotation of the device 200 about its longitudinal axis L (e.g., with the tag being mounted on a proximal side 222 of the device 200). When the device 200 has been positioned as desired, the tag may be separated from the device 200 as described above.

The inner sleeve 204 is connected to the interstitial mesh 206 via a plurality of members 238 so that the inner and outer sleeves 204, 202 are separated from one another via the annular space 228. The inner sleeve 204 extends longitudinally from a first end 240 to a second end 242 and, as described above, defines a shape substantially corresponding to a medullary canal of the target bone and has a length substantially corresponding to the distance of separation between the separated portions of bone B. As would be understood by those skilled in the art, wherein length of the outer sleeve 202 is selected to be equal to a distance between the separated portions of bone B, the inner sleeve 204 and the outer sleeve 202 with have the same length. If the outer sleeve 202 is lengthened to overlap the bone B at one or both ends of the device 200, the inner sleeve 204 will be slightly shorter than the outer sleeve 202. Connecting the inner sleeve 204 to the outer sleeve 202 only via the struts 216, 216' permits the inner sleeve 204 to float within the outer sleeve 202. Thus, when the device 200 is utilized with a target bone having an intramedullary rod M implanted therein, the inner sleeve 204 is movable relative to the outer sleeve 202 to fit the intramedullary rod M even when the intramedullary rod M is not centered in the bone B.

Since the device 200 may be custom built and printed for a specific patient, the length, circumference and shape of the outer sleeve 202 may be customized. For example, the length of the outer sleeve 202 may be selected so that, when the outer sleeve 202 is positioned in the target area about the target bone B, first and second ends 210, 212 of the outer sleeve 202 match the distance separating the portions of bone B or so that they overlap the portions of bone B by, for example, 5 mm on each side. The length of the inner sleeve 204 may be selected so that there is a clearance between the end surfaces of the separated portions of bone B by a selected distance (e.g., 2 mm at the first and second ends 240, 242 of the inner sleeve 204). It will be understood by those of skill in the art, however, that dimensions of the device 200 may be varied, as desired and suited for a specific patient. The device 200 may be formed of biodegradable polymers such as, for example, polycaprolactone (PCL), which is both printable and bioresorbable.

According to an exemplary method, the device 200 may be custom-built and printed to suit patient specific bone dimensions and needs as described above.

The device 200 which may have been previously packed with graft material may be oriented as desired (e.g., by reference to the tag with the distal side 124 of the device 100 facing the target bone in which an intramedullary rod M has been inserted. The outer sleeve 202, interstitial mesh 206 and the inner sleeve 204 may then be opened by separating spreading the device open via the slot 214. The device 200 may then be slid between the separated portions of bone B until the intramedullary rod M is received in the space 215. At this point, the device 200 may be released to permit the slot 214 to close. The surgeon may then remove the tag and open the outer sleeve 202 at the proximal side 222 of the device 200 to pack additional graft material into the space 228 via the widened slot 226. Those skilled in the art will understand that this embodiment allows the surgeon to open the device 200 via the slot 214 at the distal side 224 to slide the device 200 into position over the intramedullary rod M while permitting the surgeon to open the device 200 via the slot 226 on the proximal side of the device 200 to pack additional graft material therein without rotating the device 200. This may be especially useful in a case where the inner and or outer sleeves 204, 202, respectively, are asymmetrical from the proximal side 222 to the distal side 224. For example, as shown in FIGS. 6-9, if the distal side 224 of the device 200 is shorter than the proximal side 222 (reflecting a similar asymmetry in the separated portions of bone B), the device 200 can only be inserted distal side first which would make the distal split inaccessible for later packing of graft material. Thus, a device such as the device 200 with a distal split at the slot 214 and a proximal split at the slot 226 may be inserted distal side first to capture the intramedullary rod M and, when the device 200 has reached the desired position between the separated portions of bone B (shown in FIG. 7), the user may pack additional graft material into the device 200 in a way that would not be feasible without the proximal slot 226.

Graft material may also be inserted at the ends of the device 200, between the first and second ends 240, 242 of the inner sleeve 204 and the ends of the separated portions of bone B. Once the device 200 has been positioned as desired, the outer sleeve 202 may be closed by drawing the longitudinal edges of the outer sleeve 202 adjacent to the slots 214 and 226 toward one another and fixing these edges to one another. For example, the longitudinal edges may be sutured together to fix the device 200 in the desired position over the target bone B. Additional graft material may be packed into device via the mesh of the outer sleeve 202 after the device 200 has been positioned over the bone B, as described above.

The overlapping of the first and second ends 210, 212 over ends of the separated portions of bone B and the positioning of the inner sleeve 204 between two portions of bone B is sufficient to hold the device 200 in position over the target area of the bone B. In particular, the interstitial mesh 206 and the inner sleeve 204 help prevent migration of the device 200 along the bone B. In some cases where additional fixation is desired, however, a user (e.g., surgeon) may insert a bone fixation element (e.g., a bone screw) through one or more of the screw holes formed in the screw receiving structures 220 into the underlying bone.

In some cases, the user may desire to further customize the device 200 during the grafting process. In these cases, the user may cut portions of the device 200 to accommodate the specific needs of the patients bone. The device 200 may be formed of a material that may be cut using, for example, a scissor or other cutting tool. For example, if desired, the user may adjust a length of the outer sleeve 202 to suit a patients' specific needs and/or to create less overlap between the device 200 and the bone.

It will be understood by those of skill in the art that various modification and variations may be made in the structure and methodology of the present invention, without departing from the spirit or the scope of the invention. Thus, it is intended that the present invention cover the modifications and variations of this invention provided that they come within the scope of the appended claims and their equivalents.

What is claimed is:

1. A device for containing bone graft material, comprising:
    an outer sleeve extending longitudinally from a first end to a second end and sized and shaped to correspond to a profile of an outer surface of a target bone, the outer sleeve including a first proximal longitudinal split extending along an entire length of the outer sleeve; and
    an inner sleeve connected to the outer sleeve to define a bone graft holding space between the inner and outer sleeves, the inner sleeve sized and shaped to correspond to a profile of a medullary canal of the target bone, the device including a distal longitudinal split opening through the inner and outer sleeves to an interior of a circumference of the inner sleeve.

2. The device of claim 1, wherein the inner sleeve is connected to the outer sleeve via a plurality of first struts extending from the inner sleeve to the outer sleeve on a first side of the distal longitudinal split and a plurality of second struts extending from the inner sleeve to the outer sleeve on a second side of the distal longitudinal split opposite the first side of the distal longitudinal split.

3. The device of claim 1, wherein the inner sleeve includes a second proximal longitudinal split extending along at least a portion of a length thereof substantially opposite the distal longitudinal split to facilitate opening of the distal longitudinal split.

4. The device of claim 1, wherein the inner sleeve is connected to the outer sleeve only at the distal longitudinal split.

5. The device of claim 1, further comprising an interstitial structure including a plurality of spacing members, each of the spacing members coupled to one of the inner and outer sleeves toward the other of the inner and outer sleeves to maintain a desired spacing between the inner and outer sleeves, the spacing members being spaced from one another circumferentially around at least a portion of the inner sleeve and longitudinally along at least a portion of the length of the device to control a size of the bone graft holding space.

6. The device of claim 5, wherein the interstitial structure forms a plurality of shelves separated from one another along the length of the device to divide the bone graft holding space into a plurality of longitudinally separated graft holding spaces.

7. The device of claim 2, wherein each of the first struts is connected to a first portion of the outer sleeve via a corresponding first living hinge and each of the second struts is connected to a second portion of the outer sleeve via a corresponding second living hinge permitting the first and second portions of the outer sleeve to be rotated relative to the first and second struts to open the bone graft holding space for the insertion of bone graft material into the bone graft holding space.

8. The device of claim 7, wherein rotation of the first and second portions of the outer sleeve away from one another opens the device into a substantially W shape with the bone graft holding space open to a proximal side of the device.

9. The device of claim 1, wherein a connection between the inner sleeve and the outer sleeve is configured to permit the outer sleeve to float relative to the inner sleeve so that the outer sleeve can remain in position as desired around a target portion of bone even when an intramedullary nail received within the inner sleeve is not centered relative to the target portion of bone.

10. The device of claim 1, wherein the inner sleeve further includes at least one second living hinge formed substantially diametrically opposite the distal longitudinal split to facilitate opening of the distal longitudinal split so that the device is configured to be inserted to a target position over a previously implanted intramedullary implant.

11. The device of claim 1, wherein the outer sleeve is formed as a plurality of circumferential and longitudinal members intersecting to define openings of a predetermined size selected to retain bone graft material within the bone graft holding space.

12. The device of claim 11, wherein the inner sleeve is formed as a plurality of circumferential and longitudinal members intersecting to define openings of a predetermined size selected to retain bone graft material within the bone graft holding space.

13. The device of claim 11, wherein longitudinally adjacent ones of the openings of the outer sleeve are offset relative to one another relative to a longitudinal axis of the device.

14. The device of claim 13, wherein longitudinally adjacent ones of the openings of the inner sleeve are offset relative to one another relative to a longitudinal axis of the device.

15. The device of claim 1, further comprising a tag releasably attached to a proximal side of the device, a shape of the tag indicating a desired implantation orientation of the device.

16. A graft containment device for treating bone, comprising:
    a radially inner sleeve dimensioned and shaped to substantially match dimensions of a medullary canal of a portion of bone to be treated; and
    an outer sleeve extending circumferentially outside and around the inner sleeve to define a bone graft holding space between the inner and outer sleeves, the outer sleeve including a proximal longitudinal split along an entire length of the outer sleeve, the device including a distal longitudinal split opening from an exterior of the outer sleeve to a space within the inner sleeve so that the device is configured to be inserted to a target position in which a previously implanted intramedullary implant is received within the space within the inner sleeve while the outer sleeve extends around a space conforming to an outer surface of a portion of bone to be replaced.

17. The device of claim 16, wherein the outer sleeve is coupled to the inner sleeve so that the outer sleeve is configured to be spread open at the proximal longitudinal split for the insertion of bone graft material into the bone graft holding space and the outer sleeve may then be closed around the bone graft material to retain the bone graft material within the bone graft holding space.

18. The device of claim 17, further comprising a plurality of first struts and a plurality of second struts coupling the inner sleeve to the outer sleeve to define the bone graft holding space, a portion of the circumferences of the inner and outer sleeves being disconnected from one another and the first struts being immediately adjacent a first side of the distal longitudinal split while the second struts are separated from the first struts about a circumference of the device by a width of the distal longitudinal split so that the outer sleeve is configured to be spread apart at the first proximal longitudinal split.

19. The device of claim 16, further comprising an interstitial structure including a plurality of spacing members extending between the inner and outer sleeves and being spaced from one another longitudinally along at least a portion of a length of the device, each of the spacing members being coupled to only one of the inner and outer sleeves.

20. The device of claim 16, wherein the proximal longitudinal split is on a side of the device opposite the distal longitudinal split.

* * * * *